United States Patent [19]

Ayer et al.

[11] Patent Number: 5,141,752
[45] Date of Patent: * Aug. 25, 1992

[54] DELAYED DRUG DELIVERY DEVICE

[75] Inventors: Atul D. Ayer, Mountain View; Felix Theeuwes, Los Altos; Patrick S. L. Wong, Hayward, all of Calif.

[73] Assignee: Alza Corporation, Palo Alto, Calif.

[ * ] Notice: The portion of the term of this patent subsequent to Jun. 27, 2006 has been disclaimed.

[21] Appl. No.: 715,256

[22] Filed: Jul. 25, 1991

Related U.S. Application Data

[60] Continuation of Ser. No. 312,845, Feb. 21, 1989, Pat. No. 4,986,987, which is a division of Ser. No. 861,188, May 9, 1986, Pat. No. 4,842,867.

[51] Int. Cl.⁵ .............................................. A61K 9/24
[52] U.S. Cl. ..................................... 424/473; 424/471; 424/468
[58] Field of Search ................ 424/473, 468, 471, 472

[56] References Cited

U.S. PATENT DOCUMENTS 4,842,867 6/1989 Ayer ..................................... 424/473
4,948,592 7/1990 Ayer ..................................... 424/473

Primary Examiner—Thurman K. Page
Assistant Examiner—Raj Bawa
Attorney, Agent, or Firm—Paul L. Sabatine; Jacqueline S. Larson; Jean M. Duvall

[57] ABSTRACT

A dosage form comprising (1) an immediately available dose of a beneficial drug followed by a timed delayed dose of drug, or (2) a timed delayed dose of drug.

32 Claims, 2 Drawing Sheets

DELAYED DRUG DELIVERY DEVICE

CROSS REFERENCE TO CO-PENDING APPLICATIONS

This application is a continuation of U.S. patent application Ser. No. 07/312,845 filed Feb. 21, 1989 now U.S. Pat. No. 4,986,987 issued Jan. 22, 1991, which is a division of U.S. patent application Ser. No. 06/861,188, filed May 9, 1986, now U.S. Pat. No. 4,842,867, issued Jun. 27, 1989.

This invention pertains to a novel dosage form useful for the pulsed delivery of a beneficial drug. The dosage form, after an interval of time, can deliver a single pulse or dose of drug, or the dosage form can deliver an initial pulse or dose of drug followed by a delayed pulse or dose of drug.

BACKGROUND OF THE INVENTION

Many beneficial drugs are administered at a definite time for their beneficial effects. For example, sleeping aids that help in falling asleep are usually taken before bed and then, if needed, at a later time, say four or five hours later. Then too, the symptomatic relief of anxiety and tension, and the relief from pain and inflammation, usually requires an initial pulse or first dose supplemented at a later interval by another pulse or second dose. The pulsatile delivery of drugs having a short half-life, that is drugs that lose one-half of their therapeutic activity because the drug is metabolized or excreted, require pulsed administration at recurring intervals. Also, it is often desirable to administer a drug in a form that makes the drug available at a later time for a pulsed delivery of a drug. The need for pulsed delivery arises during a circadian or chronological cycle, for drugs with a pronounced first post effect and for drugs which on continuous low level may lead to tolerance.

Prior to this invention, drugs with short half-lives were often administered to a recipient once-or-twice in separate dosage forms during a given time span, for example one-or-two doses to obtain the benefit of the drugs pharmacokinetic activity. This type of repeated dosing is accompanied with shortcomings. For example, when a drug is administered at bed time the presently available prior art dosage forms requires repeated dosing the recipient and interrupting the sleep for the next dose. Then too, a recipient on a therapeutic program often forgets to take the next dose, and this lack of compliance leads to a drug-free interval during which interval the recipient does not get the benefit of the next needed dose.

It is immediately apparent in the light of the above presentation that a pressing need exists for a dosage form that can delay the delivery of a drug and then deliver a pulsed dose of drug. It is apparent also that a pressing need exists for a dosage form that can immediately deliver a pulsed dose of drug followed by a drug-free interval and then deliver a pulsed dose of drug. It will be appreciated by those versed in the dispensing art, that if a novel and unique dosage form is made available for executing a therapeutic program comprising pulsed and delayed drug delivery patterns, such a dosage form would have a practical application and it would also represent a valuable contribution to the medical and veterinary arts.

OBJECTS OF THE INVENTION

Accordingly, in view of the above presentation, it is an immediate object of this invention to provide a novel and useful dosage form that represents an unexpected improvement in the dispensing art and substantially overcomes the disadvantages known to the prior art.

Another object of the present invention is to provide a dosage form that can deliver a pulsed dose of a beneficial drug.

Another object of the present invention is to provide a dosage form that can delay the delivery of the drug from the dosage form, and then deliver a pulsed dose of the drug.

Another object of the present invention is to provide a novel dosage form comprising means for delivering an initial pulsed dose of drug, means for maintaining a drug-free interval, and means for delivering a later pulsed dose of drug at a later time.

Another object of the present invention is to provide a novel dosage form that overcomes the limited functionality of conventional dosage tablets, and which novel dosage form can preform a drug program comprising delivering a drug at a pulsed rate and for a pulsed duration as needed to achieve a desired therapeutic program.

Another object of the invention is to provide a dosage form comprising two doses of drug in a single dosage form that can be used for twice a day dosing of the drug.

Another object of the present invention is to provide a novel dosage form manufactured in the form of a drug delivery device comprising means for delivering a pulsed dose of drug, means for providing a drug-free interval, and means for then providing a recurring pulsed dose.

Another object of the invention is to provide a dosage form comprising two doses in a single dosage form.

Another object of the present invention is to provide a dosage form comprising an exterior member for providing an immediate pulsed dose of drug, and an internal member for providing a delayed pulsed dose of drug.

Other objects, features and advantages of the invention will be more apparent to those versed in the dispensing art from the following specification, taken in conjunction with the drawing figures and the accompanying claims.

BRIEF DESCRIPTION OF THE DRAWING FIGURES

In the drawing figures, which are not drawn to scale, but are set forth to illustrate various embodiments of the invention, the drawing figures are as follows.

In the drawing figures and in the specification, like parts in related figures are identified by like numbers. The terms appearing earlier in the specification and in the description of the drawing figures, as well as embodiments thereof, are further described elsewhere in the disclosure.

DETAILED DESCRIPTION OF THE DRAWING FIGURES

Figure 1:
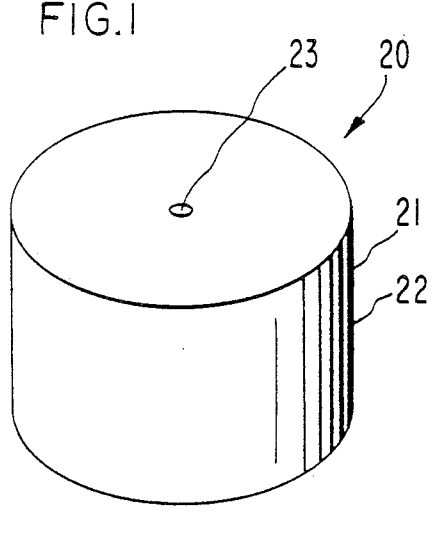
FIG. 1 is a general view of a dosage form provided by the invention, which dosage form is designed and shaped for oral administration, for delayed, or pulsed patterns of drug delivery to the gastrointestinal tract.

Turning now to the drawing figures in detail, which drawing figures are an example of the dosage form provided by the invention, and which examples are not to be construed as limiting, one example of the dosage form is illustrated in FIG. 1 and designated by the numeral 20. In FIG. 1, dosage form 20 comprises a body member 21 comprising a wall 22 that surrounds and forms an internal compartment not seen in FIG. 1. Dosage form 20 further comprises at least one exit means 23 for connecting the interior of dosage form 20 with the exterior environment of use.

Figure 2:
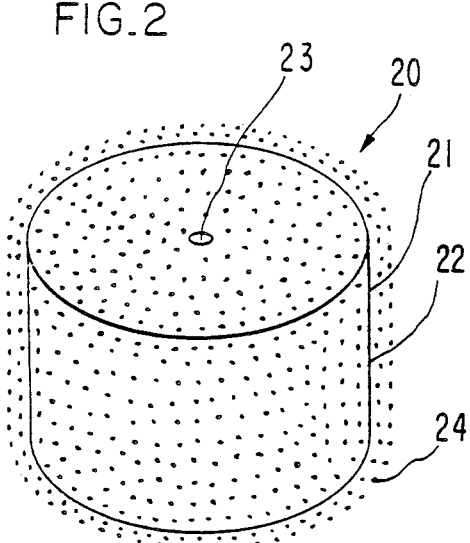
FIG. 2 is a view of an osmotic dosage form provided by the invention comprising an exterior dosage amount of drug for the initial pulsed delivery of the drug to the gastrointestinal tract.

FIG. 2 illustrates dosage form 20 of FIG. 1 comprising body 21, wall 22, exit means 23 and exterior lamina 24. Exterior lamina 24 comprises a dosage unit amount of drug for an initial pulsed dose of drug to the environment of use, the gastrointestinal tract of a warm-blooded animal. The initial pulse is the first dose of drug. Exterior lamina 24 comprises from about 0.1 to 99.9 weight percent (wt. %) of a drug, and from 99.9 to 0.1 wt. % of a pharmaceutically acceptable carrier for the drug, with the total wt. % of all lamina 24 forming members equal to 100%. In a more preferred embodiment the initial pulse dose is from 10 to 80 wt % and from 90 to 20 wt % carrier. The carrier is a means for coating the drug onto the exterior surface of the wall, and the carrier comprising lamina 24 onto the exterior surface of wall 22. In the fluid environment of use, the carrier releases the drug thereby providing the initial or first pulsed dose of the drug to the environment of use. The carrier releases the initial pulsed dose in from greater than zero time up to 1 hour, and in a presently preferred pulsed dose time of from several minutes up to 30 minutes. Typical carrier means include a hydrophilic polymer, that are in a presently preferred embodiment a member selected form the group consisting of hydroxymethyl cellulose, hydroxyethyl cellulose, hydroxypropyl cellulose, hydroxypropyl methylcellulose and hydroxypropyl ethylcellulose.

Figure 3:
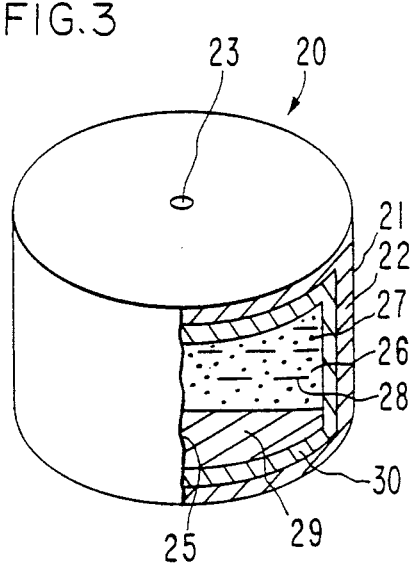
FIG. 3 is an opened view of a dosage form provided by the invention, which dosage form delays the pulsed delivery of a dose amount of drug to the gastrointestinal tract.

FIG. 3 is a view of dosage form 20 seen in opened view with wall 22 sectioned at 25 for illustrating the internal structure of dosage form 20. In FIG. 3, osmotic dosage form 20 comprises body 21, wall 22 that surrounds and defines an interior compartment 26 and at least one exit means 23. Wall 22 of dosage form 20 comprises at least in part, or totally, a composition that is permeable to the passage of an exterior fluid present in the environment of use, and it is substantially impermeable to the passage of drug and other ingredients present in compartment 26. Wall 22 is comprised of a polymeric composition that is inert and maintains its physical and chemical integrity during the life time of dosage form 20. The phrase, "physical and chemical integrity" denotes wall 22 does not lose its structure and it does not change during the dispensing life of dosage form 20. Typical materials for forming wall 22 comprise selectively semipermeable polymers known to the art as osmosis and reverse osmosis polymers. These polymeric compositions comprise a cellulose ester, cellulose ether, cellulose ester-ether, cellulose acylate, cellulose diacylate, cellulose triacylate, cellulose acetate, cellulose diacetate, and cellulose triacetate. In a presently preferred embodiment wall 22 is a composition comprising cellulose acetate having an acetyl content of 32%, cellulose acetate having an acetyl content of 39.8%, hydroxypropyl methylcellulose and polyethylene glycol. In one example wall 22 is a composition comprising from 15 to 45 wt. % cellulose acetate having an acetyl content of 32%; 15 to 45 wt. % cellulose acetate having an acetyl content of 39.8%; from 5 to 35 wt. % of hydroxypropyl methylcellulose; and from 5 to 35 wt. % polyethylene glycol 3350.

Internal compartment 26 in one preferred embodiment houses a first layer comprising a beneficial drug formulation 27, identified by dots, and a hydrogel carrier 28, identified by dashes, for drug formulation 27. Hydrogel carrier means 28 comprises a hydrophilic composition that is noncross-linked, or lightly cross-linked, and it possesses the ability to form a dispensable, pulsed drug formulation by homogeneously blending with drug formulation 27. In operation, hydrogel carrier means 28 absorbs and/or imbibes fluid and expands to form a dispensable pulsed formulation that is released from dosage form 20 transporting drug formulation 27 therewith. The pulsed dose has generally a pulsed duration of 10 minutes to 200 minutes, and more preferably 20 minutes to 40 minutes. Generally, the dosage unit amount of drug blended with the hydrogel carrier means is about 1 to 80 wt. %.

Internal compartment 26 houses a second layer 29 comprising a hydrogel member and in a presently preferred embodiment in osmagent blended with the hydrogel member. The hydrogel comprising second layer 29 exhibits fluid absorbing and/or fluid imbibing properties. The hydrogel comprised of a hydrophilic polymer interacts with water and aqueous biological fluids and swells or expands to an equilibrium state. The hydrogel exhibits the ability to swell in aqueous fluid and retain a significant portion of the absorbed or imbibed fluid within the polymer structure. In operation, the first layer and the second layer cooperate to deliver the drug formulation from dosage form 20. In operation, the second layer 29 absorbs fluid, expands and exerts pressure against the first layer. Simultaneously, the first layer absorbs fluid and forms a dispensable formulation. By the combined operation of the first and second layers, with the second layer expanding against the first layer and urging it from the compartment, and with the first layer forming a dispensable formulation, the drug formulation is delivered from the dosage form.

The hydrogel composition comprising carrier means 28 and second layer 29 swell or expand to a very high degree, usually exhibiting from their nonhydrated state a 2 to 50 fold increase in volume. The hydrogel comprising carrier means 28, for the purpose of this invention, is a different hydrogel than the hydrogel comprising second layer 29. The hydrogel comprising carrier means 28 and the hydrogel comprising second layer 29, in operation, cooperate to deliver the pulsed dose of drug from the dosage form. Representative hydrophilic hydrogels consists of a member selected from the group consisting of poly(hydroxyalkyl methacrylate) having a molecular weight of 20,000 to 5,000,000; poly(vinylpyrrolidone) having a molecular weight of about 10,000 to 360,000; poly(vinyl alcohol) having a low acetate content and lightly cross-linked with glyoxal, formaldehyde, glutaraldehyde and having a degree of polymerization from 200 to 30,000; poly(ethylene oxide) having a molecular weight form 10,000 to 5,000,000; acidic carboxy polymers known as carboxypolymethylene and carboxyvinyl polymers, a polymer consisting of acrylic acid lightly cross-linked with pollyallyl-sucrose and sold under the trademark Carbopol ®, acidic carboxy polymer having a molecular weight of 200,000 to 6,000,000, including sodium acidic carboxyvinyl hydrogel and potassium acidic carboxyvinyl hydrogel; Cyanamer ® polyacrylamide; and the like. The representative polymers are known to the art in *Handbook of Common Polymers,* by Scott and Roff, published by the Chemical Company, Cleveland, Ohio; *ACS Symposium Series,* No. 31, by Ratner and Hoffman, pp. 1 to 36, 1976, published by the American Chemical Society; and in *Recent Advances In Drug Delivery Systems,* by Schacht, pp. 259 to 278, published by Plenum Press. N.Y.

Second layer 29 can comprise optionally an osmagent blended with the hydrophilic polymer. The osmagent is present to aid in imbibing exterior fluid through wall 22 and into second layer 29. The dual action of the osmagent imbibing fluid and the hydrogel imbibing fluid results in an increase in the expansion of layer 29 thereby assuring substantially complete delivery of drug formulation 27 from dosage form 20. Osmagents are known also as osmotically effective solutes and osmotically effective compounds. The osmagents are soluble in fluid that enters the dosage form, and they exhibit an osmotic pressure gradient across semipermeable wall 22 against an exterior fluid. Osmotically effective osmagents useful for the present purpose include magnesium sulfate, magnesium chloride, sodium chloride, lithium chloride, potassium sulfate, sodium sulfate, sodium carbonate, lithium sulfate, sodium sulfate, and the like. The osmagent is usually present as a particle, powder, granule, or the like. The amount of active osmagent homogeneously or heterogeneously blended with the hydrophilic hydrogel in the second layer is usually form 0.01% to 45%, or higher. The osmotic pressure in atmospheres, ATM, of the osmagent suitable for the invention will be greater than zero ATM, generally from zero ATM up to 500 ATM, or higher. The osmotic pressure of an osmagent is measured in a commercially available osmometer that measures the vapor pressure difference between pure water and the solution to be analyzed, and according to standard thermodynamic principles the vapor pressure ratio is converted into an osmotic pressure difference. The osmometer used for the present measurements is identified as Model 1001-A Vapor Pressure Osmometer, manufactured by Knauer and distributed by Utopia Instrument Co., Joliet, Ill.

Dosage form 20 of FIG. 3 comprises internal delayed coat 30 that surrounds the first layer and the second layer. Delayed coat 30 is a drug-free coat. Delayed coat 30 provides an interval of time during which dosage form 20 postpones the delivery of drug formulation 27. Delayed coat 30 in its initial dry state is about 0.1 mm to 10 mm thick, and in a more presently preferred range delayed coat 30 is about 4 to 7 mm thick. Delayed coat 30 is a means for delaying the delivery of drug formulation for about 1 hour to 12 hours, preferably 2 hours to 9 hours, and in a presently more preferred embodiment it provides a drug-free interval of 3 hours to 6 hours.

Delayed coat 30 comprises initially a dry hydrophilic polymer such as a member selected from the group consisting of hydroxypropyl methylcellulose, hydroxypropylcellulose, methylcellulose, carboxymethylcellulose, hydroxyethylcellulose, hydroxymethylcellulose, and the like. Delayed coat 30 can comprise also a member selected from the group consisting of poly(oxyethylene), poly(vinyl pyrrolidone), carboxyvinyl polymer, and the like.

Figure 4:
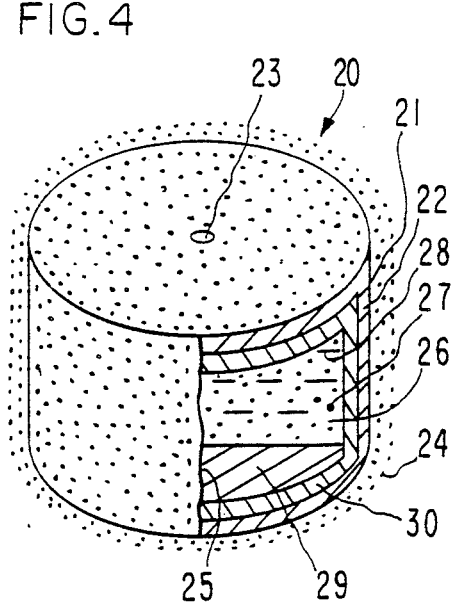
FIG. 4 is an opened view of a dosage form provided by the invention which dosage form provides an initial pulsed dose of drug followed by a drug-free interval and then another pulsed dose of drug; and, FIG. 5 is an opened view of another embodiment of the invention for providing a first dose of drug and at a later time a second dose of drug.

FIG. 4 illustrates another dosage form 20 provided by the invention. Dosage form 20 makes available the pulsed delivery of drug followed by a drug-free interval, and then a final pulsed dose of drug. This dosage form also exemplifies a single dosage form comprising two distinct and independent doses of drug. Dosage form 20 of FIG. 4 comprises exterior pulsed drug coat 24 that surrounds in at least a part exterior wall 22 of body 21 of dosage form 20. Dosage form 20 also comprises an exit passageway 23 that communicates the exterior of dosage form 20 with internal compartment 26. Internal compartment 26 comprises a first layer that comprises drug formulation 27 and carrier means 28, and a second layer comprising a hydrogel composition 29. An inner positioned delayed, drug-free coat 30 is located between the inside surface of wall 20 and it surrounds both inner contacting layers in compartment 26. Dosage form 20, is sized, shaped and designed for oral admittance into the gastrointestinal tract of a warm-blooded animal including a human. Dosage form 20 is manufactured as an osmotic device and it provides a pulsed-delayed-pulsed drug pattern or first dose delay second dose in the manner described for the above drawing figures.

Figure 5:
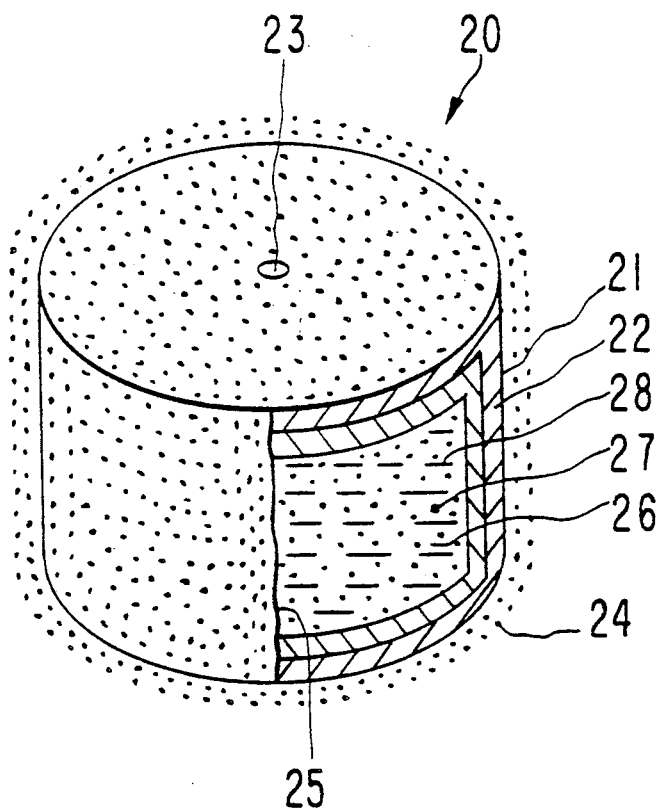

FIG. 5 illustrates another dosage form 20 provided by the invention. Dosage form 20 of FIG. 5 comprises body 21, wall 22 comprising at least in part a semipermeable composition, which wall is sectioned at 25, exit means 23, exterior lamina 24 comprising a first dosage amount of drug, interior drug release delaying lamina 30, internal compartment 26 housing a second dosage amount of orally administrable drug 27 and, optionally, a hydrogel 28.

The expression "exit means" as used herein comprises means and methods suitable for releasing the pulsed dose from compartment 26. The expression includes at least one passageway or orifice that passes through wall 22 for communicating with compartment 26. The expression "at least one passageway" includes aperture, orifice, bore, pore, porous element through which drug can migrate, a hollow fiber, capillary tube and the like. The expression includes also a material that erodes or is leached from wall 22 in the fluid environment of use to produce at least one passageway in the dosage form. Representative materials suitable for forming at least one passageway, or a multiplicity of passageways include an erodible poly(glycolic) or poly(lactic) acid member in the wall, a gelatinous filament, leachable materials such as fluid removable pore forming polysaccharides, salts or oxides, and the like. A passageway or a plurality of passageways can be formed by leaching a material such as sorbitol from the wall to produce a controlled release passageway. The passageway can have any shape, such as round, triangular, elliptical, and the like. The device can be constructed with one or more passageways in spaced apart relation on more than a single surface of a dosage form. Passageways and equipment for forming passageways are disclosed in U.S. Pat. Nos. 3,916,899; 4,063,064 and 4,088,864. Passageways of controlled dimensions formed by leaching are disclosed in U.S. Pat. No. 4,200,098.

The expression "drug formulation", as used herein, denotes any beneficial agent, compound, or composition of matter, that can be delivered by the dosage form in pulsed doses or first and second doses to produce a beneficial, therapeutic results. The drugs for the present purpose include any physiologically or pharmacologically active substance that produces a local or a systemic effect in animals. The term animals includes warm-blooded mammals, humans, primates, household, sport, farm and zoo animals. The term "physiologically" as used herein denotes the administration of a drug to produce normal levels and functions. The term "pharmacologically" denotes variations in responses to various amount of drug administered to the host. *Stedman's Medical Dictionary*, 1966, published by Williams and Wilkins, Baltimore, Md. The active drugs that can be delivered include inorganic and organic drugs without limitations, drugs that can act on the central nervous system, depressants, hypnotics, sedatives, psychic energizers, tranquilizers, anticonvulsants, muscle relaxants, antiparkinson agents, anti-inflammatories, local anesthetics, muscle contractants, antimicrobials, antimalarials, hormonal agents, contraceptives, diuretics, sympathomimeters, antiparasitics, neoplastics, hypoglycemics, ophthalmics, electrolytes, diagnostics, cardiovascular drugs, and the like. The beneficial drugs are known to the art in *Pharmaceutical Sciences*, by Remington, 14 Ed., 1979 published by Mack Publishing Co., Easton, Pa.; *The Drug, The Nurse, The Patient, Including Current Drug Handbook*, 1974-76 by Falconer et al., published by Sounder Company, Philadelphia, Pa.; and *Physician's Desk Reference*, 40th Ed., 1986, published by Medical Economics Co., Oradell, N.J.

The wall of the dosage form, and the exterior pulsed release lamina can be formed in one technique using the air suspension procedure. This procedure consists in suspending and tumbling delayed, coated bilayers in a current of air and a wall forming, or outer pulsed lamina composition, until in either operation the wall or the pulsed lamina is applied to the delayed coated bilayers. The air suspension procedure is well-suited for independently forming the wall of the pulsed lamina. The air suspension procedure is described in U.S. Pat. No. 2,799,241; in *J. Am. Pharm. Assoc.*, Vol. 48, pp. 451 to 459, 1959; and, ibid, Vol. 49, pp. 82 to 84, 1960. The osmotic dosage-pulsed-delayed systems can also be coated with the wall forming composition, or the lamina pulsed composition with a Wurster ® air suspension coater, using for example methylene dichloride—methanol cosolvent. The aeromatic ® air suspension coater can be used also employing a cosolvent. Other wall and laminating techniques such as pan coating can be used for providing the dosage form. In the pan coating system the wall forming, or the pulsed lamina forming, compositions are deposited by successive spraying of the composition on the delayed coated bilayers accompanied by tumbling in a rotating pan. A pan coater is used to produce a thicker wall or lamina. A larger volume of methanol can be used in a cosolvent to produce a thinner wall or lamina. Finally, the wall or lamina coated compartments are dried in a forced an oven at 50° C. for a week, or in a temperature and humidity controlled over for 24 hours at 50° C. and 50 relative humidity, to free the dosage form of solvent. Generally, the wall formed by these techniques have a thickness of 2 to 20 mils with a presently preferred thickness of 4 to 10 mils. The exterior pulsed dose lamina generally will have a thickness of 0.5 to 15 mils, usually 0.5 to 7.5 mils.

Exemplary solvents suitable for manufacturing the wall or the lamina include inert inorganic and organic solvents that do not adversely harm the wall, the lamina and the final dosage system. The solvents broadly include a member selected form the group consisting of an alcohol, ketone, ester, ether, aliphatic hydrocarbon, halogenated solvents, cycloaliphatic solvents, aromatic, heterocyclic, aqueous solvents, and mixtures thereof.

The dosage form of the invention is manufactured by standard techniques. For example, in one manufacture the beneficial drug and other ingredients comprising the first layer facing the exit means are blended and pressed into a solid layer. The layer possesses dimensions that correspond to the internal dimensions of the area the layer is to occupy in the dosage form and it also possesses dimensions corresponding to the second layer for forming a contacting arrangement therewith. The drug and other ingredients can be blended also with a solvent and mixed into a solid or semisolid form by conventional methods such as ballmilling, calendering, stirring or rollmilling and then pressed into a preselected shape. Next, a layer of hydrogel is placed in contact with the layer of drug in a like manner. The layering of the drug formulation and the hydrogel layer can be fabricated by conventional two-layer press techniques. The two contacted layers are first coated with a delayed drug-free overcoat and then with the outer wall. The drug-free delayed composition can be applied by press coating, molding, spraying, dipping, and air suspension procedures. The air suspension and air tumbling procedure comprises in suspending and tumbling the pressed, contacting first and second layers in a current of air containing the delayed-forming composition until the first and second layers are surrounded by the delayed composition.

In another manufacture, the dosage form is manufactured by the wet granulation technique. In the wet granulation technique the drug and the ingredients comprising the first layer are blended using an organic cosolvent, such as isopropyl alcohol-methylene dichloride 80/20 v/v (volume/volume) as the granulation fluid. The ingredients forming the first layer are individually passed through a 40 mesh screen and then thoroughly blended in a mixer. Next, other ingredients comprising the first layer are dissolved in a portion of the granulation fluid, the cosolvent described above. Then, the latter prepared wet blend is slowly added to the drug blend with continual mixing in the blender. The granulating fluid is added until a wet blend is produced, which wet mass blend is then forced through a 20 mesh screen onto oven trays. The blend is dried for 18 to 24 hours at 35° C. in a forced air oven. The dried granules are then sized with a 20 mesh screen. Next, magnesium stearate is added to the dry screened granule blend, and this blend passed through an 80 mesh screen. The granulation is then put into milling jars and mixed on a jar mill for 5 to 10 minutes. The composition is pressed into a layer, for example in a 3-station Manesty ® layer press. The speed of the press is set at 30 rpm and the maximum load set at 2 tons. The first layer is pressed against the composition forming the second layer and the bilayer tablets are fed to the Kiliam ® dry Coata press and surrounded with the drug-free coat followed by the exterior wall solvent coating.

Another manufacturing process that can be used for providing the compartment-forming composition comprises blending the powdered ingredients in a fluid bed granulator. After the powdered ingredients are dry blended in the granulator, a granulating fluid, for example poly(vinylpyrrolidone) in water, is sprayed onto the powders. The coated powders are then dried in the granulator. This process granulates all the ingredients present therein while adding the granulating fluid. After the granules are dried, a lubricant such as stearic acid or magnesium stearate is added to the granulator. The granules are then pressed in the manner described above.

DESCRIPTION OF EXAMPLES OF THE INVENTION

The following examples are merely illustrative of the present invention and they should not be considered as limiting the scope of the invention in any way, as these examples and other equivalents thereof will become more apparent to those versed in the art in the light of the present disclosure, the drawing figures and the accompanying claims.

EXAMPLE 1

A dispensing device is manufactured for delivery a beneficial drug as follows: a first layer and a second layer are compressed in contacting arrangement in a three layer press under a 1½ ton pressure head. The first layer is made from granules of a homogeneous master blend comprising 570 g of polyethylene oxide having a molecular weight of 200,000; 400 g of midazolam; and 30 g of hydroxypropylmethyl cellulose. The ingredients are dry blended, then wetted with 350 ml of anhydrous ethanol, followed by drying in an oven for 17 to 20 hrs at 30° C. The dry granules then are passed through a 30 mesh screen. The second layer is formed from a composition comprising 650 g of polyethylene oxide having a molecular weight of 5,000,000; 290 g of sodium chloride; 50 g of hydroxypropylmethyl cellulose; and 10 g of ferric oxide. The materials comprising the second layer are blended and then wetted with 950 ml of anhydrous ethanol. The wet granules are dried at 30° C. for 15 to 20 hrs in a forced air oven, and then passed through a 20 mesh sieve.

The granules for the first layer forming composition are transferred to the number 1 hopper, and the granules for the second layer forming composition are added to the number 2 hopper of the press. The first and second layers are pressed together with the first layer weighing 12.5 mg and the second layer weighing 50.0 mg, with a diameter of 4.76 mm.

A delay layer coating is applied with a Kilian ® dry Coata press. The pressed together layers are transferred to the Coata press hopper, and a delay composition comprising hydroxypropyl cellulose is dry coated around the first and second layers. The delay coated first and second layers have a diameter of 7 mm.

Next, the delayed coated layers are transferred to an Aeromatic ® air suspension coater. The systems are surrounded with a semipermeable wall-forming composition for applying a 4 mg wall per system. The wall forming composition comprises 30 wt. % cellulose acetate having an acetyl content of 39.8%; 30 wt. % cellulose acetate having an acetyl content of 32%; 20 wt. % polyethylene glycol 400; and 20 wt. % hydroxypropyl methyl cellulose. The wall forming ingredients are dissolved in a cosolvent comprising methylene chloride: methanol (85:15 wt. %) to obtain 5% solids.

Finally, a first and a second passageway are drilled through the wall for connecting the exterior o the dosage form with the interior of the dosage form. A passageway is drilled on two distant surfaces of the dosage form. The dosage forms are dried in a forced air oven at 50° C. for 40 hrs to remove all residual solvent. The dosage forms are sized and shaped for oral admittance into the gastrointestinal tract of a human.

EXAMPLE 2

The procedure of Example 1 is repeated in this example with all manufacturing steps as previously set forth, except that in this example the wall comprising the semipermeable composition is coated with a pulsed coat of drug. The pulsed coat is applied to the exterior surface of the wall from a composition comprising 50 wt. % midazolam, 25 wt. % hydroxypropyl cellulose and 25 wt. % tartaric acid, dissolved in distilled water to obtain 15 wt % solids. The pulsed coat applied to each dosage form contains 10 mg of midazolam.

Next, a pair of passageways were drilled through the outermost pulsed coat and the wall for connecting the exterior of the wall for connecting the exterior of the dosage form with its compartment. The dosage form is dried as described previously.

The dosage form prepared according to the example releases the 100 mg of midazolam in about 10 minutes. The first pulsed release is followed by a 3½ hour drug-free period. The second dose of midazolam is delivered in about ½ hour for 80% of the drug with substantially all of the drug delivered in about 1 to 1½ hours.

EXAMPLE 3

The procedures of Examples 1 and 2 are repeated in this example. In this example, the first layer weighed 18.75 mg, the second layer weighed 70 mg, the internal delay layer weighed 110 mg, the wall weighted 4.5 mg and the outermost coat contained 15 mg of midazolam. The dosage form released 15 mg of midazolam in a first 15 minute pulsed period, and delivered 7.5 mg of midazolam after a 3.5 hour delay.

EXAMPLE 4

The procedure of Example 1 is followed for manufacturing a dosage form comprising two 6.5 mil (0.17 mm) passageways on two opposite surfaces of the dosage form. The dosage form delivered the internally housed midazolam after a 3.5 hour delay with 80% delivered in about ½ hour.

EXAMPLE 5

The procedures of Examples 1 and 4 are followed that the interior housed delayed composition comprises hydroxypropylmethyl cellulose 47.5 wt %; hydroxypropyl cellulose 50 wt. % and polyvinyl pyrrolidone 2.5 wt. %.

EXAMPLES 6 and 7

The above procedure is repeated with the manufacturing conditions as set forth, with one example comprising an internal delay layer weighing 80 mg that release the drug after 2.8 hours; and another internal delay coat weighing 120 mg that permits the dosage form to deliver the drug after a 4.6 hour delay period of time.

EXAMPLE 8

A dosage form for use as a nighttime sleep-aid comprising an exterior pulsed dose of diphenhydramine hydrochloride, and an internal pulsed dose of diphenhydramine is made as follows: a first layer comprising 50 mg of diphenhydramine hydrochloride, polyethylene oxide having a molecular weight of 120,000 and hydroxypropylmethyl cellulose, is pressed in contacting position to a second layer comprising polyethylene oxide having a molecular weight of 5,000,000 and sodium chloride. The two layers are first surrounded with a delay coat comprising hydroxypropyl cellulose, and then with a wall comprising cellulose triacetate having an acetyl content of 43.5% and cellulose acetate having an acetyl content of 32%. The wall is coated on its outer surface with an instant pulsed dose coat comprising 25 mg of diphenhydramine hydrochloride, hydroxypropyl cellulose and citric acid. The dosage form is made with a pair of spaced-apart passageways. The dosage form is administered one at bed time for the relief of sleeplessness. The dosage form delivers the outer pulsed dose and after a 3 to 3½ hour drug-free period, delivers the internal dose. The dosage form is blister packed for ease of administration.

EXAMPLE 9

The procedure of Example 8 is repeated with the condition as described previously except that in this example the dosage form internally contained in the first layer 15 mg of doxylamine succinate, and 10 mg of doxylamine succinate in the exterior coat. The dosage form is administered about 30 minutes before retiring as nighttime sleep aid.

EXAMPLE 10

A dosage form for the relief of menstrual pain and more particularly menstrual and premenstrual pain and discomfort is made in accordance with the above described procedures. The dosage form comprises an internal first layer comprising 200 mg of acetaminophen, 34 mg of pamabrom (2-amino-2-methyl-1-propanol-8-bromo-theophyllinate), and 17 mg of pyriliamine maleate, polyethylene oxide having a molecular weight of 120,000 and hydroxypropylmethyl cellulose, a second layer comprising Cyanamer ® A-370 a hydrogel polyacrylamide of about 200,000 molecular weight, and sucrose; and an outermost exterior pulsed coat comprising 100 mg of acetaminophen, 16 mg of pamabrom and 8 mg of pyrilamine maleate. The dosage form after administration delivers an instant pulse dosage amount followed by repeated dosage amount of the beneficial drugs 3 to 4 hours later. The dosage form provided by the invention comprises within a single dosage form a first dose and a repeat dose substantial equivalent to multiples of twice, thrice a day or the like.

EXAMPLE 11

A dosage form comprising dimenhydrinate indicated for the prevention and the treatment of nausea, vomiting or vertigo of motion sickness is prepared according to the procedure of Example 100. The dosage form comprises 50 mg of dimenhydrinate in the first layer and 50 mg of dimenhydrinate in the outer pulsed dose. The dosage form is indicated for preventing motion sickness by taking the dosage form ½ to 1 hour before starting the activity, thereby providing a first instant dose followed by a repeat dose 3 to 4 hours later from the same dosage form.

EXAMPLE 12

A dosage form comprising two independently administrable doses with the administration of a first dose followed by the administration of a second dose at a later time from the same, single dosage form is made according to the above procedures. In this example, the dosage form comprises an internal 5 mg dose of methamphetamine hydrochloride, an anoretic for use in obesity, in the first layer, and 5 mg of the same anoretic in the outermost first dose coat. The dosage form can be administered once a day taken one-half hour before a meal, usually before breakfast or lunch.

EXAMPLE 13

A dosage form for use as a nightime cough relief up to 12 full hours is manufactured as described in Example 8. The dosage form of this example comprises two doses in a single dosage form indicated for convenient b.i.d. dosing that helps quiet coughs during the night. The exterior first dose of the dosage form comprises 15 mg of dextromethorphan HBr, and the later delivered second does comprises 15 mg of dextromethorphan HBr. The dosage form is administered orally on retiring for substantially avoiding interrupted rest.

EXAMPLE 14

A single dosage form comprising two distinct and timed separate doses useful for administering the antihistamine chlorprophenpyridamine maleate is manufactured as described above. The dosage form comprises an immediately timed released external first dose comprising 6 mg of chlorprophenpyridamine and a later timed released second dose comprising 6 mg of chlorprophenpyridamine for producing approximately ten hours symptomatic antihistamine relief to the recipient.

EXAMPLE 15

A dosage form for use as a sleep-aid is provided by following the above manufacture procedures. The dosage form of this example comprises an internal compartment 26, drug formulation 27 comprising 60 mg of diphenhydramine hydrochloride and 340 mg of polyethylene oxide having a molecular weight of 10,000. The drug formulation 27 is surrounded with a delay lamina comprising hydroxypropyl cellulose and then with a lamina comprising cellulose acetate having an acetyl content of 32%. An exterior lamina for providing an instant pulse dosage of 20 mg of diphenhydramine hydrochloride, hydroxypropyl cellulose and adipic acid. The dosage form comprises a first and a second passageway, and when in operation it provides an instant first dose followed by delayed second dose delivered 3 to 3½ hours later.

EXAMPLE 16

The above procedures are followed in this example for manufacturing a dosage form comprising a first pulse of 0.15 mg of the sedative triazolam and a later time delayed second pulse of 0.1 mg of triazolam.

In summary, it will be readily appreciated that the present invention contributes to the art an unobvious dosage form manufactured as a drug delivery device possessing wide and practical application. While the invention has been described and pointed out in detail and with reference to operative embodiments thereof, it will be understood that those skilled in the art will appreciate that various changes, modifications, substitutions and omissions can be made without departing form the spirit of the invention. It is intended, therefore, that the invention embrace those equivalents within the scope of the claims which follow.

I claim:

1. A dosage form for delivering a beneficial drug formulation to an environment of use, the dosage form comprising:
   (a) a wall comprising at least in part a semipermeable composition permeable to the passage of an external fluid present in the environment of use and substantially impermeable to the passage of a beneficial drug formulation, which wall surrounds and forms;
   (b) a compartment;
   (c) a drug formulation in the compartment that exhibits an osmotic pressure gradient across a semipermeable wall, which drug formulation produces at least one of a physiological, pharmacological, local and systemic effect in an animal;
   (d) means for delaying the delivery of the drug formulation up to 12 hours from the compartment, which means comprises a drug-free lamina that surrounds the drug formulation; and,
   (e) at least one exit means in the wall for communicating the exterior of the dosage form with the compartment for delivering the dosage formulation from the dosage form.

* * * * *